US012778638B2

(12) United States Patent
Wang

(10) Patent No.: US 12,778,638 B2
(45) Date of Patent: Nov. 3, 2026

(54) SYSTEM AND METHOD FOR ALIGNING VERTEBRAE IN THE CORRECTION OF SPINAL DEFORMITIES

(71) Applicant: Xiaoyu Wang, Saint-Bruno (CA)

(72) Inventor: Xiaoyu Wang, Saint-Bruno (CA)

( * ) Notice: Subject to any disclaimer, the term of this patent is extended or adjusted under 35 U.S.C. 154(b) by 41 days.

(21) Appl. No.: 19/060,662

(22) Filed: Feb. 22, 2025

(65) Prior Publication Data

US 2026/0248534 A1 Aug. 27, 2026

(51) Int. Cl.
*A61B 17/70* (2006.01)
*A61B 17/88* (2006.01)

(52) U.S. Cl.
CPC ........ *A61B 17/7004* (2013.01); *A61B 17/701* (2013.01); *A61B 17/705* (2013.01); *A61B 17/7052* (2013.01); *A61B 17/8869* (2013.01)

(58) Field of Classification Search
CPC . A61B 17/7004; A61B 17/701; A61B 17/705; A61B 17/7049; A61B 17/7052
USPC .................................................. 606/250–251
See application file for complete search history.

(56) References Cited

U.S. PATENT DOCUMENTS 9,956,009 B1 * 5/2018 Shoshtaev .......... A61B 17/7082
2016/0128734 A1 * 5/2016 Barlett ............... A61B 17/7052 606/264
2018/0070994 A1 * 3/2018 Leff .................... A61B 17/7079
2020/0146727 A1 * 5/2020 Harper ............... A61B 17/7043

* cited by examiner

*Primary Examiner* — Eduardo C Robert
*Assistant Examiner* — Christina Negrellirodriguez

(57) ABSTRACT

A system for aligning vertebrae to correct spinal deformities, comprising two transverse arms translating on two elongate bodies coupled by a gear pair mounted on a center body with revolute joints and ratchet units. The transverse arms and center body are connected to one side of the spine with three telescopic arms using three end-effectors. Auxiliary arms and end-effectors are available to connect the system to the other side of the spine. Coronal plane deformity is corrected by manipulating the angle between the elongate bodies with two manipulating handles to translate the apex of the spinal curve toward the midline of the patient; adjusting the lengths of the telescopic and auxiliary arms to correct the sagittal and transverse plane deformities. The end-effector positions are locked by engaging the ratchet units to keep the achieved corrections while the spinal rods are fixed on the spine through bone-implants.

8 Claims, 18 Drawing Sheets

A circled letter represent a subassembly
Letter "J" indicates a joint/joint axis A letter “f” in the subscript indicates a geometric feature A letter "f" in the subscript indicates a geometric feature
A letter "J" indicates a joint/joint axis A letter "f" in the subscript indicates a geometric feature A letter "f" in the subscript indicates a geometric feature A letter "f" in the subscript indicates a geometric feature A letter "f" in the subscript indicates a geometric feature A letter “f” in the subscript indicates a geometric feature

SYSTEM AND METHOD FOR ALIGNING VERTEBRAE IN THE CORRECTION OF SPINAL DEFORMITIES

CROSS-REFERENCE TO RELATED APPLICATIONS

None.

BACKGROUND OF THE INVENTION

The present invention relates to apparatus and method for correction of spinal deformities, such as scoliosis and hyperkyphosis.

Posterior spinal instrumentation is a main treatment option for severe spinal deformity manifested with an abnormal spinal curve. It uses two spinal rods precontoured to have the same shape as a normal spinal curve. The rods are attached to the left and right side of the spine, respectively, using bone implants. The bone implants generally feature a saddle-like head and a set screw. The rod can be connected to the implant and free to rotate around and translate along its lengthwise axis. The rod can be fixed on the implant by tightening the set screw. Initial curve correction is achieved as the rods are connected to but not fixed on the implants. Further correction is achieved by manipulating relative position and orientation between the spine, the rods, and the implants. The instrumentation is completed by fixing the spinal rods to all implants.

In the course of connecting the rod to implants and during the corrective manipulations, mechanical stresses in the rod evolve temporally and spatially. A major challenge not yet successfully addressed in the prior arts is that the rod can deform far beyond its elastic limit due to transient overload, especially when the spinal curve is very stiff, resulting in loss of intraoperative correction, compromised spinal rod fatigue strength, and even an inability to achieve adequate deformity correction.

There is a need for a solution to reduce the risk of material yielding of the spinal rod in the course of spinal deformity correction.

SUMMARY OF THE INVENTION

This Summary is provided to explain the essential concepts of the present invention; details are provided in the Detailed Description. It is not intended to identify key features or essential features of the claims, nor is it intended to limit the scope of the claims.

The present invention seeks to provide a solution to reduce the risk of material yielding of the spinal rod in the course of spinal deformity correction. The underlying principle is that the spinal rod will not be used until the abnormal spinal curve has been corrected and maintained by a system, and there has been substantial post-correction spinal stress relaxation.

In one embodiment of applicant's present invention, a system is provided for aligning vertebrae to correct an abnormal spinal curve, maintaining intraoperative correction as spinal stresses relax, and bearing reaction forces of the spine as a spinal rod is connected to and fixed on bone implants.

The system comprises a primary motion unit, three telescopic arms, and three end-effectors. The primary motion unit comprises a center body, two elongate bodies, and two transverse arms. The two elongate bodies are respectively connected on the center body with a revolute joint and coupled by a gear pair of a gear ratio of one to constrain their rotations with respect to the center body to be equal and in the opposite directions. Each elongate body is also connected to the center body with a ratchet unit which has an operating handle to be used to engage or disengage the ratchet. The elongate bodies are free to rotate with respect to the center body when both ratchet units are disengaged. When engaged, one ratchet prevents the rotation of the elongate bodies about the center body in one direction; the other ratchet prevents the rotation of the elongate bodies about the center body in the other direction. The elongate bodies each feature a manipulating handle. The primary spinal deformity connection motion is generated in the coronal plane by pushing the two manipulating handles toward each other or pulling them away from each other to change the angle between the two elongate bodies. The two transverse arms are respectively mounted on the two elongate bodies with a prismatic or helical joint enabling the system to be adjusted to the size of the individual spinal curve.

The center body and the two transverse arms are respectively connected to the three telescopic arms which are connected to one side of the spinal column at three locations using three end-effectors, respectively. The motion generated by the primary motion unit corrects the coronal spinal deformity by translating the apex of the coronal spinal curve toward the midline of the patient. The lengths of the telescopic arms are respectively adjusted with three controlling screws to correct the spinal deformity in the sagittal plane.

The system includes one to three auxiliary arms and additional end-effectors which are connected to the other side of the spinal column in the same manner as the primary telescopic arms. The auxiliary arms are respectively connected to the primary telescopic arms with an interconnector. The auxiliary arms are also telescopic and their lengths are respectively adjusted with adjusting screws. Differential adjusting of the lengths of the auxiliary arms with respect to the lengths of the primary telescopic arms corrects the spinal deformity in the transverse plane.

Once the desired correction is achieved, the two ratchet units are engaged to lock the positions of the end-effectors so as to keep the achieved correction for an appropriate time to allow substantial spinal stress relaxation to occur. In the meantime, the spinal rods are contoured to the corrected spinal shape and inserted and locked onto the bone-implants while the system bears all the reaction forces from the spine. The system is disconnected from the spine after the spinal rods are locked onto all the bone-implants and significant spinal stress relaxation is believed to has occurred.

DETAILED DESCRIPTION OF THE INVENTION

Detailed description of the Invention is provided through the presentation of an embodiment of the present invention. The embodiment is chosen in order to best explain the working principles of the invention and its applications and practical uses. The embodiment is not to limit the invention to the particular form disclosed.

In the following, purely for convenience, certain terminology is used and is not to be taken as a limitation on the invention. The terminology includes the words and terms specifically mentioned, derivatives thereof, and words and terms of similar import.

Figure 1:
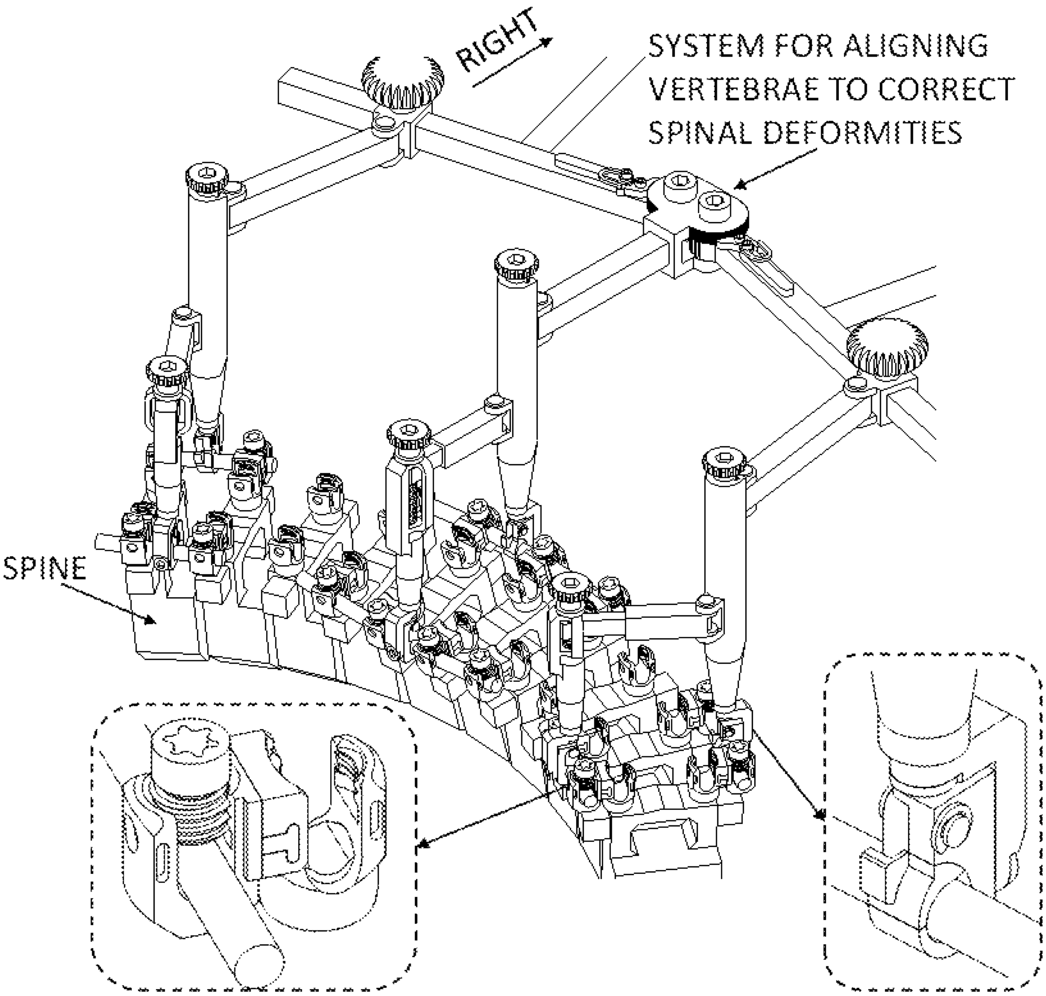
FIG. 1—Perspective view of the assembly of the system for aligning vertebrae in the correction of spinal deformities.

With reference to FIG. 1, the system is connected to one side or two sides of the spinal column.

Figure 2:
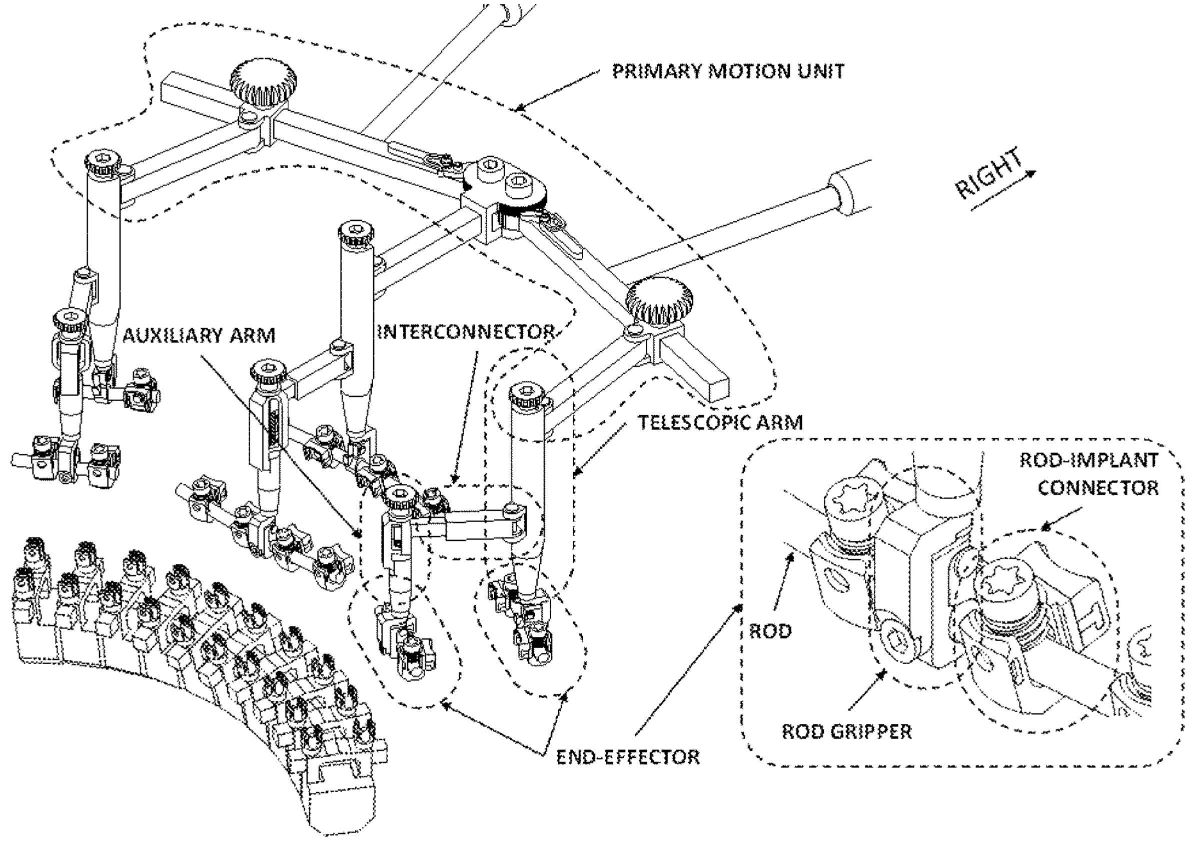
FIG. 2—Major components of the system for aligning vertebrae in the correction of spinal deformities.

With reference to FIG. 2, the system comprises a primary motion unit, three telescopic arms, three end-effectors, and additional auxiliary arms, interconnectors, and end-effectors.

Figure 3:
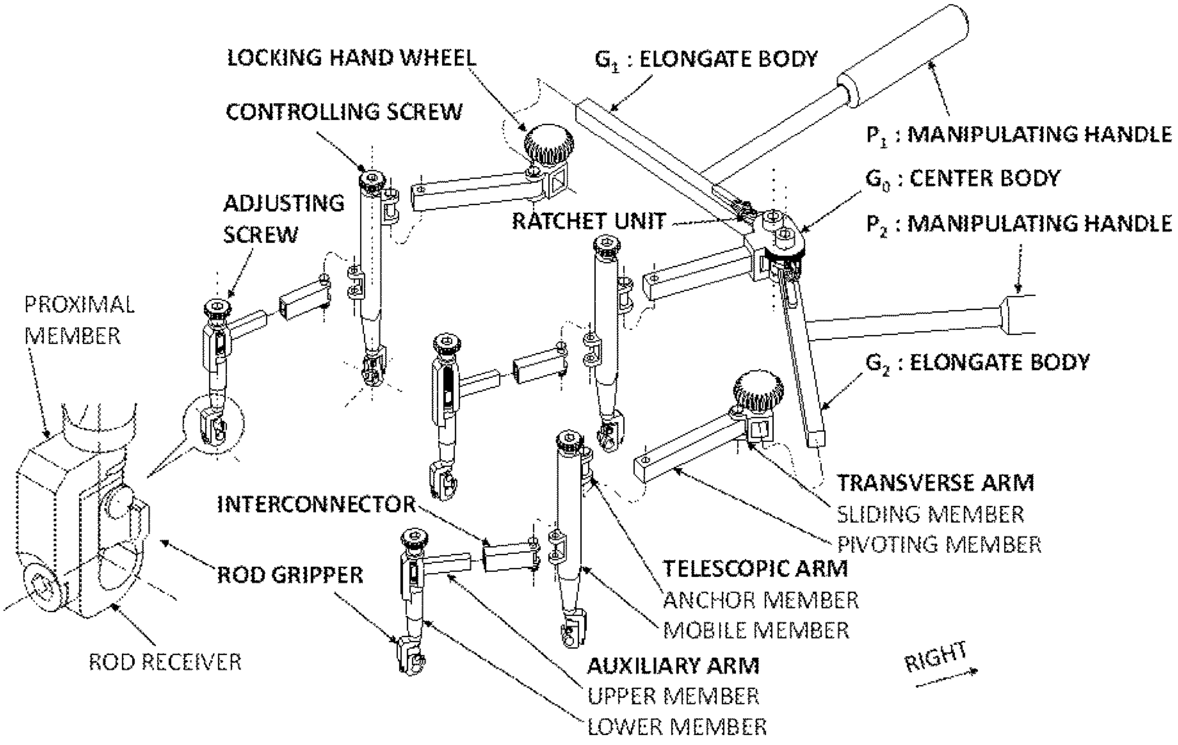
FIG. 3—Key components of the system for aligning vertebrae in the correction of spinal deformities.

With reference to FIG. 3, the primary motion unit comprises a center body, two elongate bodies each featuring a manipulating handle, two ratchet units, and two transverse arms. Each transverse arm comprises a sliding member, a pivoting member, and a locking screw with a locking hand wheel. Each telescopic arm comprises an anchor member and a mobile member as well as a controlling screw featuring a hand wheel. The auxiliary arm comprises an upper member, a lower member, and an adjusting screw with a hand wheel. The rod gripper comprises a proximal member and a receiving jaw.

Figure 4:
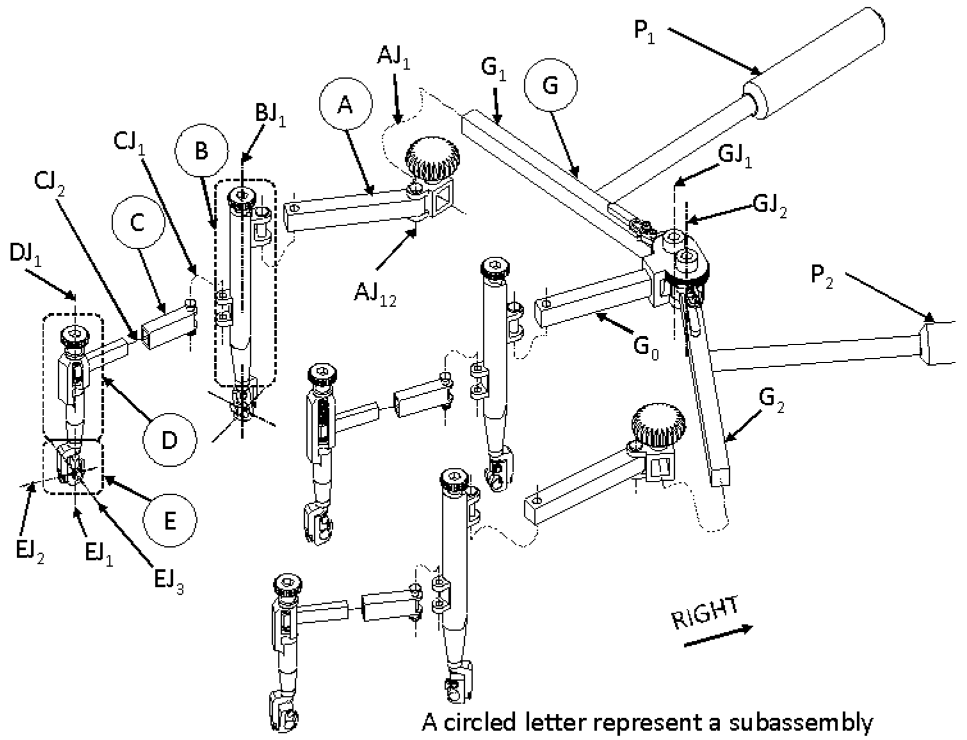
FIG. 4—Schematic perspective view of the kinematic joint groups associated with the key components of the system for aligning vertebrae in the correction of spinal deformities.
Figure 4:
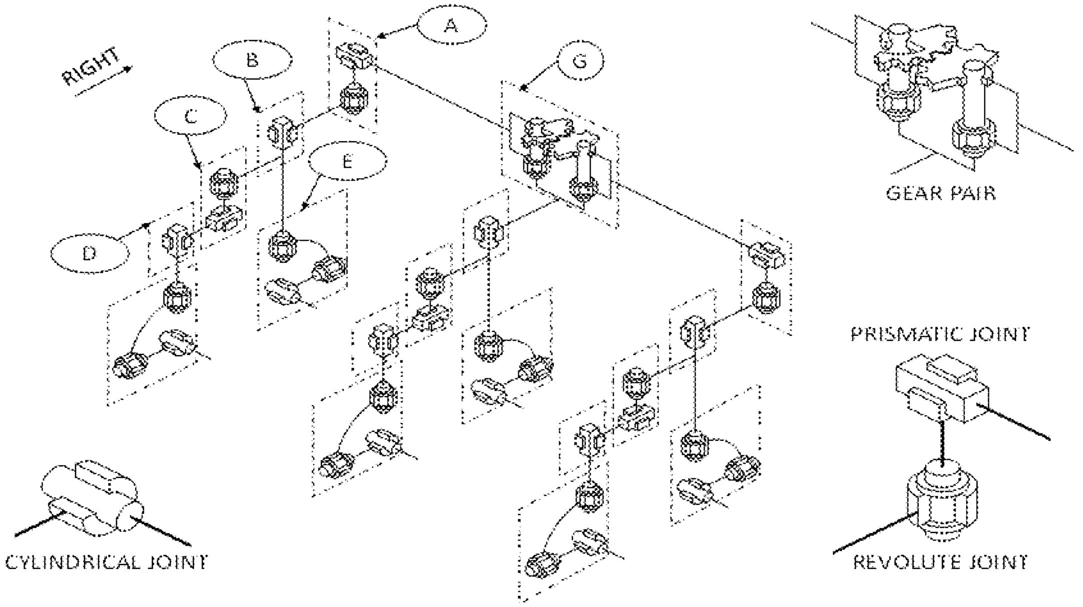

With reference to FIG. 4, the kinematic joint group (G) corresponds to connections between the two elongate bodies and the center body, comprising two revolute joints couple by a gear pair. Group (A) corresponds to connections to the transverse arm, comprising a prismatic joint and a revolute joint where the prismatic joint can be replaced with a helical joint. Group (B) corresponds to the telescopic arm having a single prismatic joint which can be replaced with a helical joint. Group (C) corresponds to the interconnector, comprising a revolute joint and a prismatic joint. Group (D) corresponds to the auxiliary arm, having a single prismatic joint which can be replaced with a helical joint. Group (E) corresponds to the rod gripper, comprising two revolute joints as well as a cylindrical joint between the rod gripper and the rod.

Figure 5:
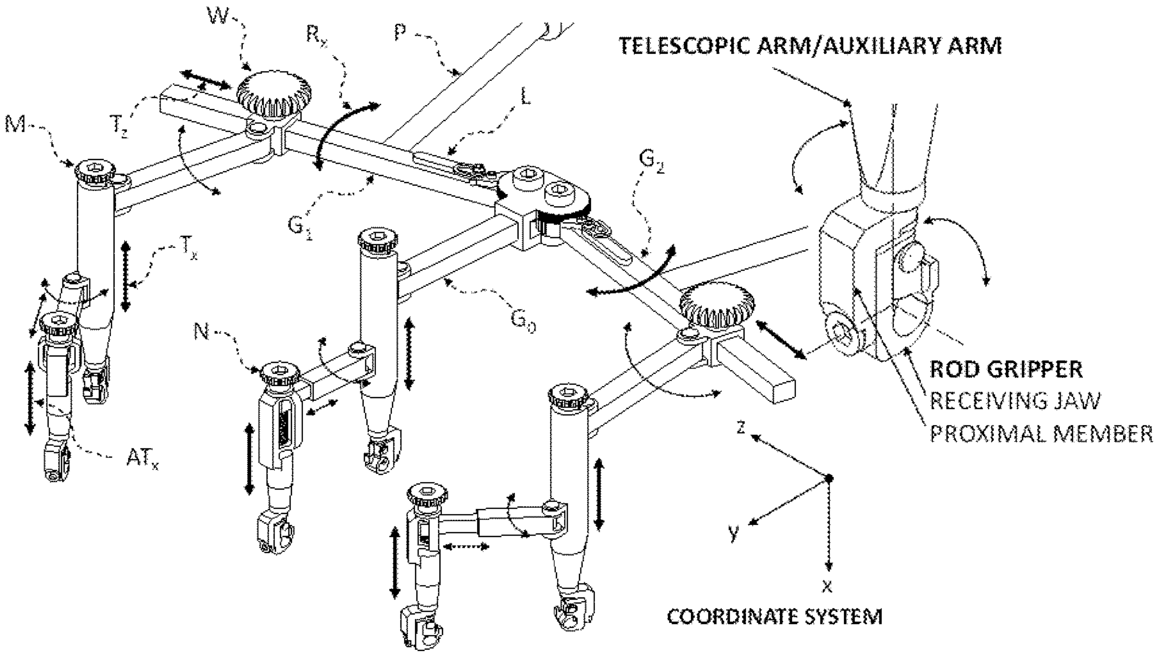
FIG. 5—Illustration of relative displacements between components of the system for aligning vertebrae in the correction of spinal deformities.

With reference to FIG. 4 and FIG. 5, the kinematic joint group (G) enables a relative rotation $R_x$ of the two elongate bodies in the yz-plane of the coordinate system. The group (A) enables a translation $T_z$ of the transverse arm along the elongate body which can be locked with the locking hand wheel W, and a rotation of the transverse arm in the yz-plane. The group (B) enables a translation $T_x$ of the mobile member of the telescopic arm along the x-axis which is controlled with the hand wheel M. The group (C) enables a rotation and a translation of the auxiliary arm with respect the telescopic arm in the yz-plane. The group (D) enables a translation $AT_x$ of the lower member of the auxiliary arm relative to its upper member along the x-axis which is controlled with the hand wheel N. The group (E) enables a 2-degree-of-freedom rotation of the receiving jaw of the rod gripper with respect to the telescopic or auxiliary arm.

Figure 6:
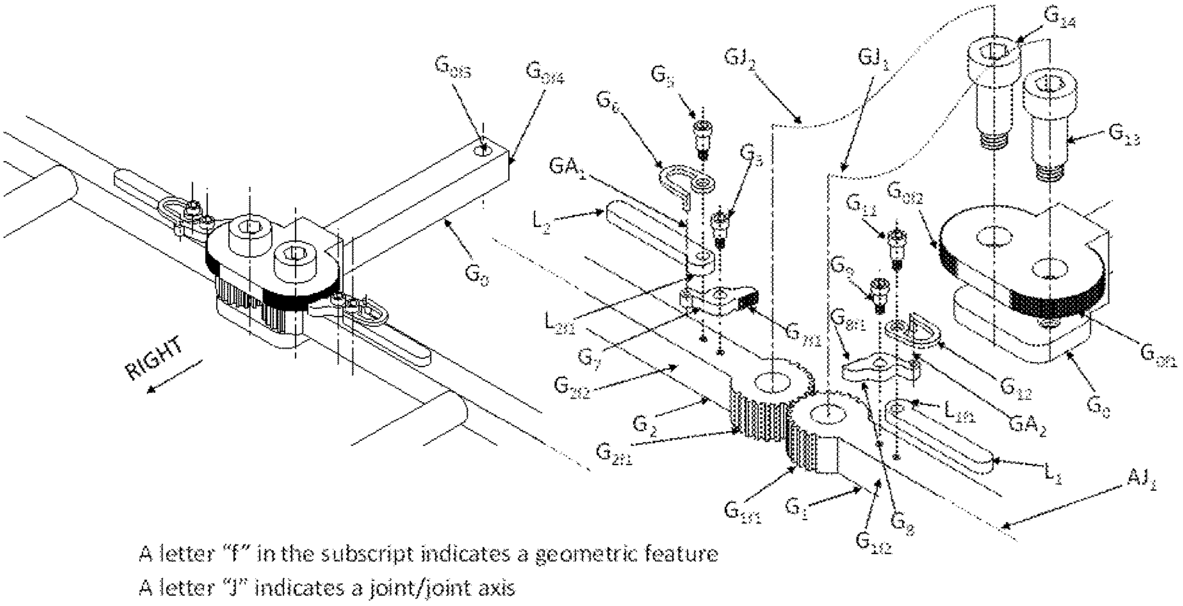
FIG. 6—Exploded perspective view of the assembly of the center body and the two elongate bodies.
Figure 7:
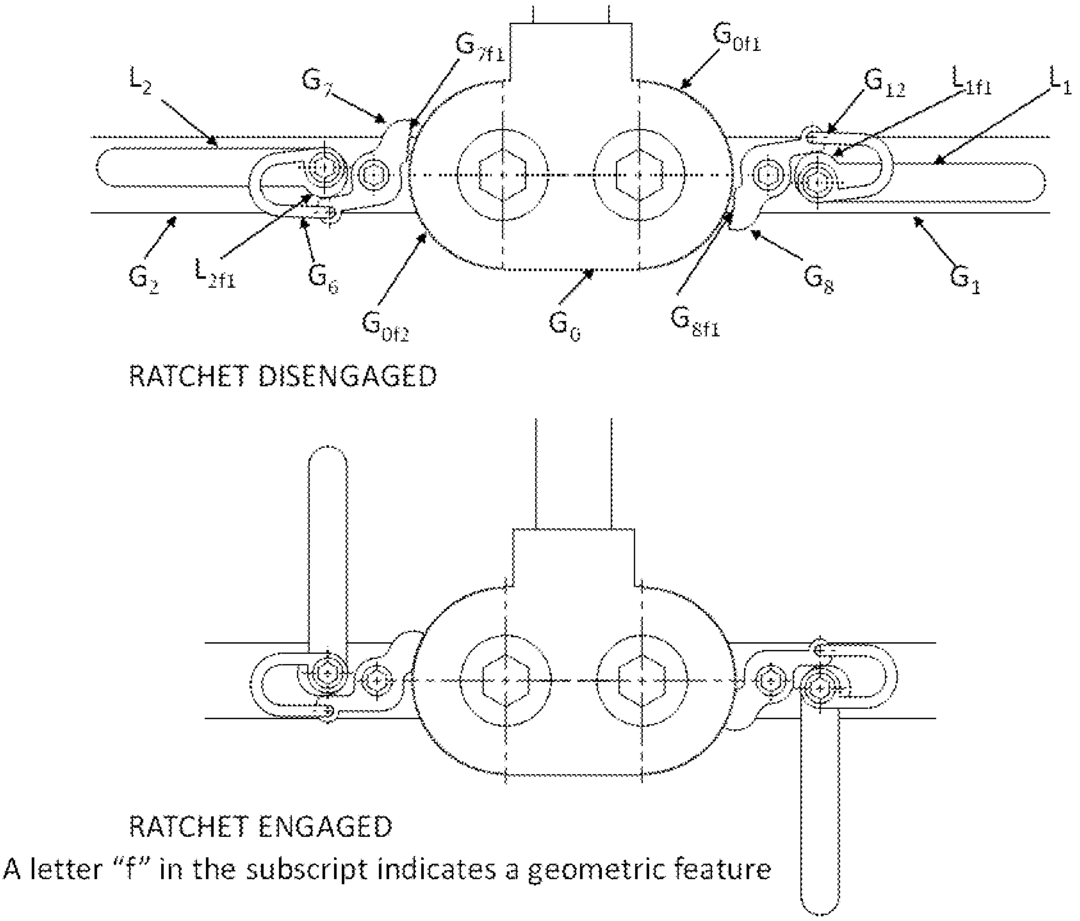
FIG. 7—Top view of the assembly of the center body and the two elongate bodies.

With reference to FIG. 6 and FIG. 7, the elongate bodies $G_1$ and $G_2$ are connected to the center body $G_0$ with two revolute joints through pins $G_{13}$ and $G_{14}$ whose axes of rotation are $GJ_1$ and $GJ_2$, respectively. The elongate bodies $G_1$ and $G_2$ are coupled by sector gears $G_{1f1}$ and $G_{2f1}$ with $GJ_1$ and $GJ_2$ as their axes. The elongate bodies $G_1$ and $G_2$ are also each connected to the center body $G_0$ with a ratchet unit. The ratchet pawls $G_8$ and $G_7$ are pivotally mounted on the elongate bodies $G_1$ and $G_2$ with pins $G_9$ and $G_3$, respectively. The camming levers $L_1$ and $L_2$ are pivotally mounted on the elongate bodies $G_1$ and $G_2$ with pins $G_{11}$ and $G_5$, respectively. The U-shaped springs $G_{12}$ and $G_6$ are pivotally mounted on the elongate bodies $G_1$ and $G_2$ with pins $G_{11}$ and $G_5$, respectively. The U-shaped springs $G_{12}$ and $G_6$ are pivotally engaged with the ratchet pawls $G_8$ and $G_7$ around the axes $GA_2$ and $GA_1$, respectively. Pressures exerted by the U-shaped springs $G_{12}$ and $G_6$ keep the ratchet pawls $G_8$ and $G_7$ in contact with the camming surfaces $L_{1f1}$ and $L_{2f1}$ on levers $L_1$ and $L_2$. The ratchet pawls $G_8$ and $G_7$ features multiple teeth $G_{8f1}$ and $G_{7f1}$ which are shaped and sized to match the ratchet gear teeth $G_{0f1}$ and $G_{0f2}$ on the center body $G_0$. When the camming levers $L_1$ and $L_2$ are turned to be aligned with the elongate bodies $G_1$ and $G_2$, the teeth $G_{8f1}$ and $G_{7f1}$ on the ratchet pawls $G_8$ and $G_7$ are cammed away from and disengaged with the teeth $G_{0f1}$ and $G_{0f2}$ on the center body $G_0$; the angle between the elongate bodies $G_1$ and $G_2$ can be manipulated by pulling away from each other or pushing toward each other the two manipulating handles $P_1$ and $P_2$ on the elongate bodies (FIG. 3). When one of the camming levers $L_1$ or $L_2$ is turned clockwise to be perpendicular to its corresponding elongate body, the teeth on the corresponding ratchet pawl is engaged with the ratchet gear teeth on the center body $G_0$ under the pressure from the U-shaped spring; the elongate body can only be turned around the center body $G_0$ in one direction. In the same manner, rotation of the elongate body around the center body $G_0$ in the other direction is blocked when the other lever is turned to be perpendicular to its corresponding elongate body.

Figure 8:
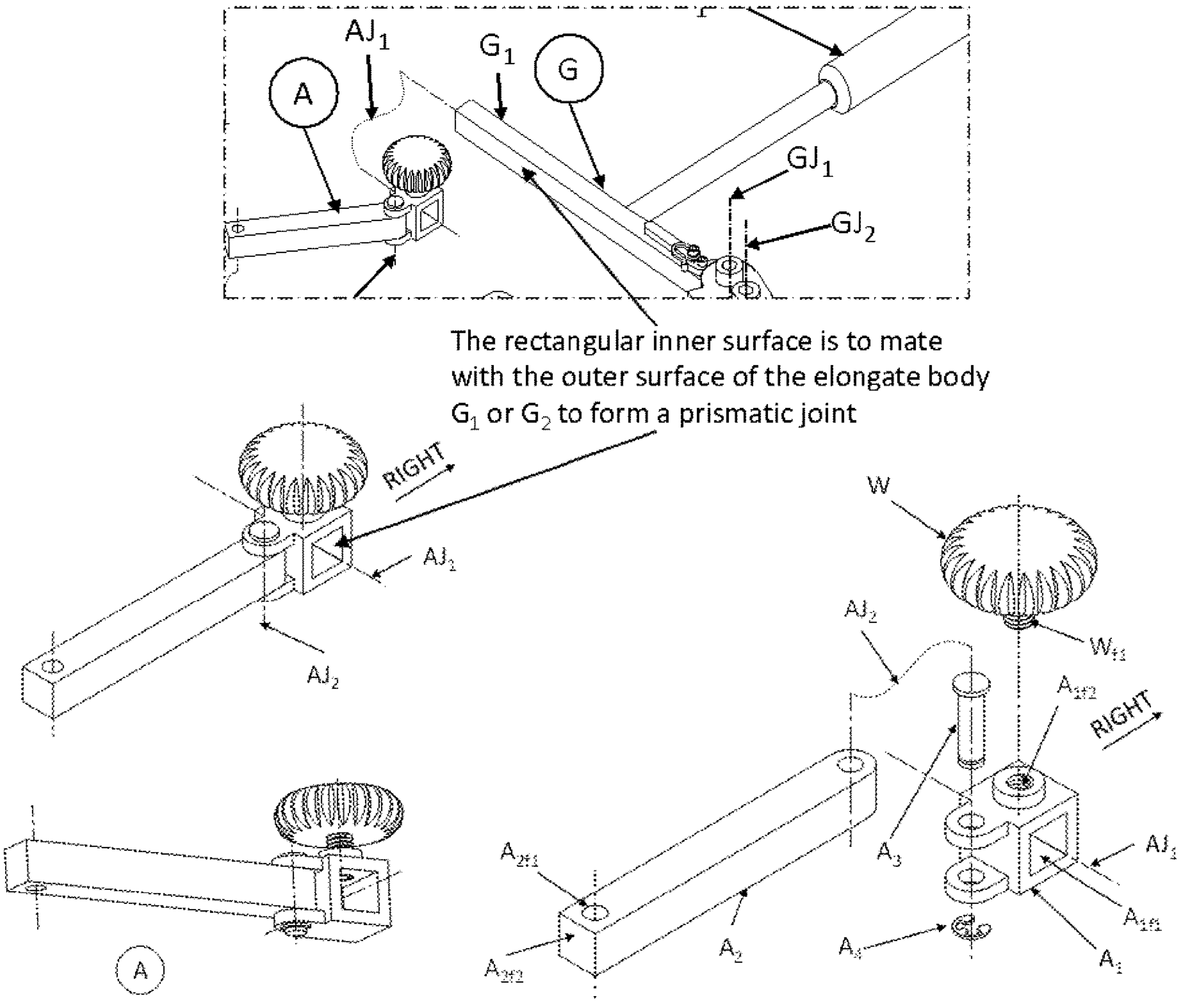
FIG. 8—Perspective view of the assembly of the transverse arm.

With reference to FIG. 8, the sliding member $A_1$ of the transverse arm is connected to the pivoting member $A_2$ of the transverse arm with a revolute joint around the axis $AJ_2$ through pin $A_3$ and retaining ring $A_4$. The sliding member $A_1$ of the transverse arm is connected to the elongate body $G_1$ with a prismatic joint along the axis $AJ_1$ through a clearance fit between the inner surface $A_{1f1}$ of the sliding member $A_1$ and the outer surface $G_{1f2}$ of the elongate body $G_1$ (FIG. 6). It is understood that the prismatic joint can be replace with a helical joint to fulfil the same function. The locking hand wheel W features a threaded cylindrical protrusion $W_{f1}$ which is in a clearance fit with the threaded hole $A_{1f2}$ of the sliding member $A_1$. Turning clockwise the locking hand wheel W locks the sliding member of the transverse arm on the elongate body $G_1$.

Figure 9:
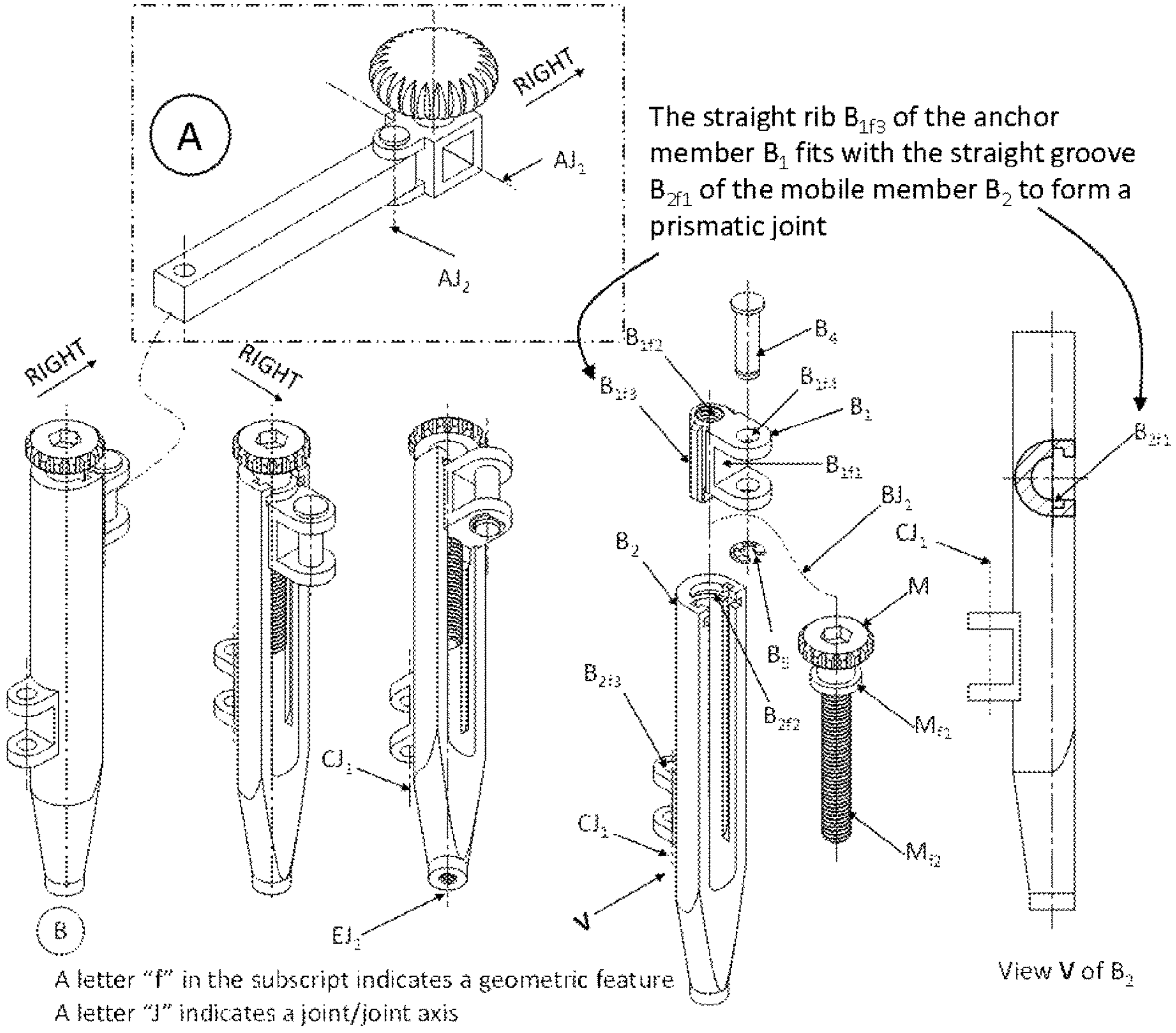
FIG. 9—Perspective view of the assembly of the telescopic arm.

With reference to FIG. 9, the anchor member $B_1$ of the telescopic arm is connected to the mobile member $B_2$ of the telescopic arm with a prismatic joint along the axes $BJ_1$ through a clearance fit between the straight rib $B_{1f3}$ of the anchor member $B_1$ and the straight groove $B_{2f1}$ of the mobile member $B_2$. It is understood that the prismatic joint can be replaced with a helical joint to fulfil the same function. The controlling screw M features a circular rib $M_{f1}$ which is in a clearance fit with a circular groove $B_{2f2}$ in the mobile member $B_2$, forming a revolute joint. The threaded portion of the controlling screw W is in a clearance fit with the threaded hole $B_{1f2}$ of the anchor member $B_1$. Turning the hand wheel on the controlling screw M translates the mobile member $B_2$ with respect to the anchor member $B_1$ along the axis $BJ_1$. The anchor member $B_1$ of the telescopic arm is connected to the pivoting member $A_2$ of the transverse arm with a fixed joint through the fit of the pin $B_4$ with the hole $B_{1f4}$ of $B_1$, hole $A_{2f1}$ of $A_2$ (FIG. 8), retaining ring $B_5$, and the contact between the flat surface $B_{1f1}$ of $B_1$ and the flat surface $A_{2f2}$ of $A_2$ (FIG. 8). The anchor member $B_1$ of the telescopic arm is connected to the center body $G_0$ of the primary motion unit (FIG. 6) with a fixed joint through the fit of the pin $B_4$ with the hole $B_{1f4}$ of $B_1$, hole $G_{0f3}$ of $G_0$ (FIG. 6), retaining ring $B_5$, and the contact between the flat surface of $B_{1f1}$ of $B_1$ and the flat surface $G_{0f4}$ of $G_0$ (FIG. 6).

Figure 10:
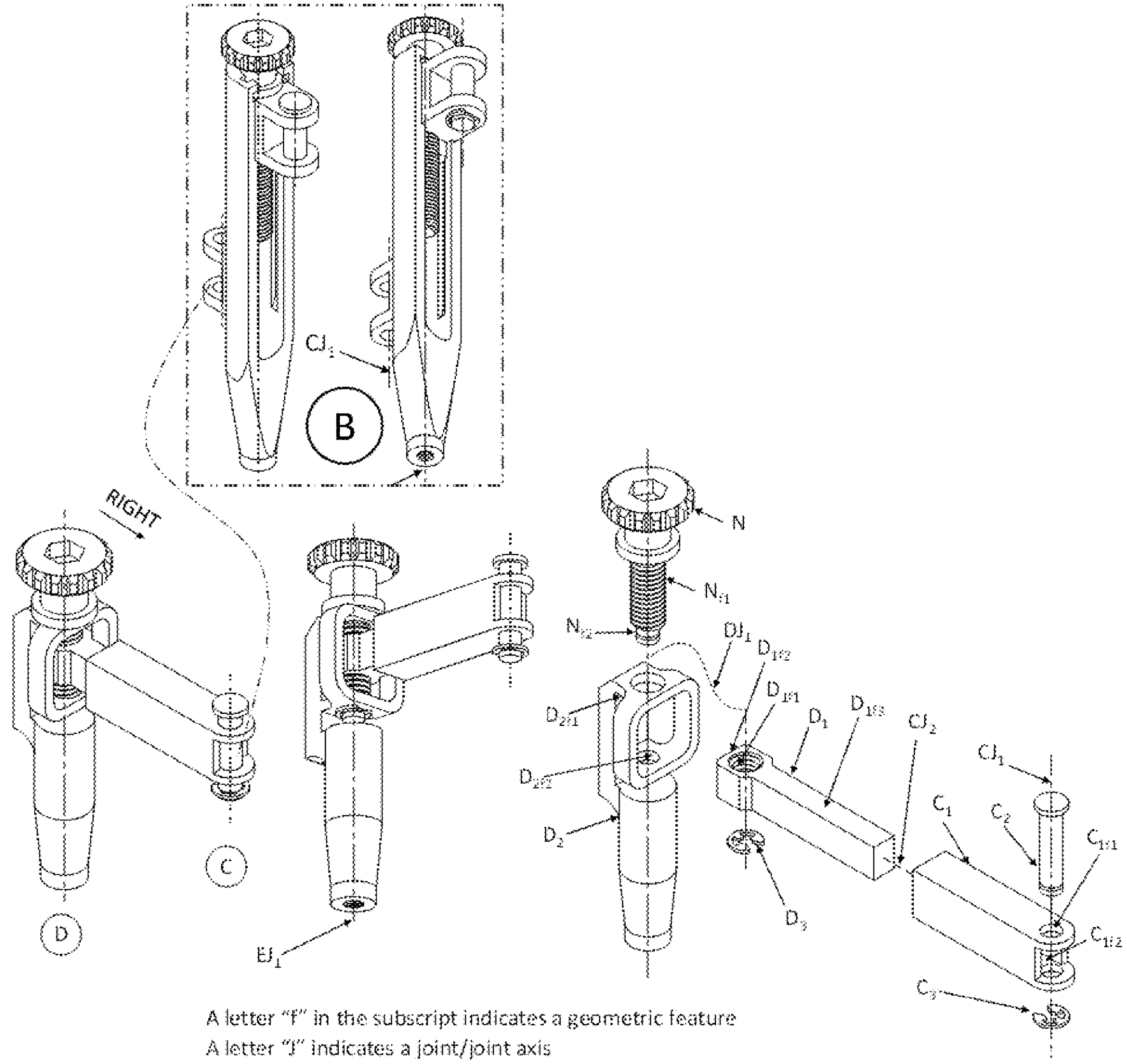
FIG. 10—Perspective view of the assembly of the auxiliary arm.

With reference to FIG. 10, the interconnector $C_1$ is connected to the mobile member $B_2$ of the telescopic arm (FIG. 9) with a revolute joint around the axis $CJ_1$ through the fit of the pin $C_2$ with the hole $C_{1f1}$ of $C_1$, hole $B_{2f3}$ of $B_2$ (FIG. 9), and the retaining ring $C_3$. The interconnector $C_1$ is connected to the upper member $D_1$ of the auxiliary arm with a prismatic joint along the axis $CJ_2$ through a clearance fit between the inner surface $C_{1f2}$ of $C_1$ and the outer surface $D_{1f3}$ of $D_1$. The upper member $D_1$ of the auxiliary arm is connected to the lower arm $D_2$ of the auxiliary arm with a prismatic joint along the axis $DJ_1$ through the contact between the flat surface $D_{1f2}$ of $D_1$ and the flat surface $D_{2f1}$ of $D_2$, and the fit of the adjusting screw N with the threaded hole $D_{1f1}$ of $D_1$, the hole $D_{2f2}$ of $D_2$, and the retaining ring $D_3$; these fits also form a helical joint between the adjusting screw N and the upper member $D_1$. It is understood that this prismatic joint can be replaced with a helical joint to fulfil the same function. Turning the hand wheel on the adjusting screw N translates the lower member $D_2$ with respect to the upper member $D_1$ along the axis $DJ_1$.

Figure 11:
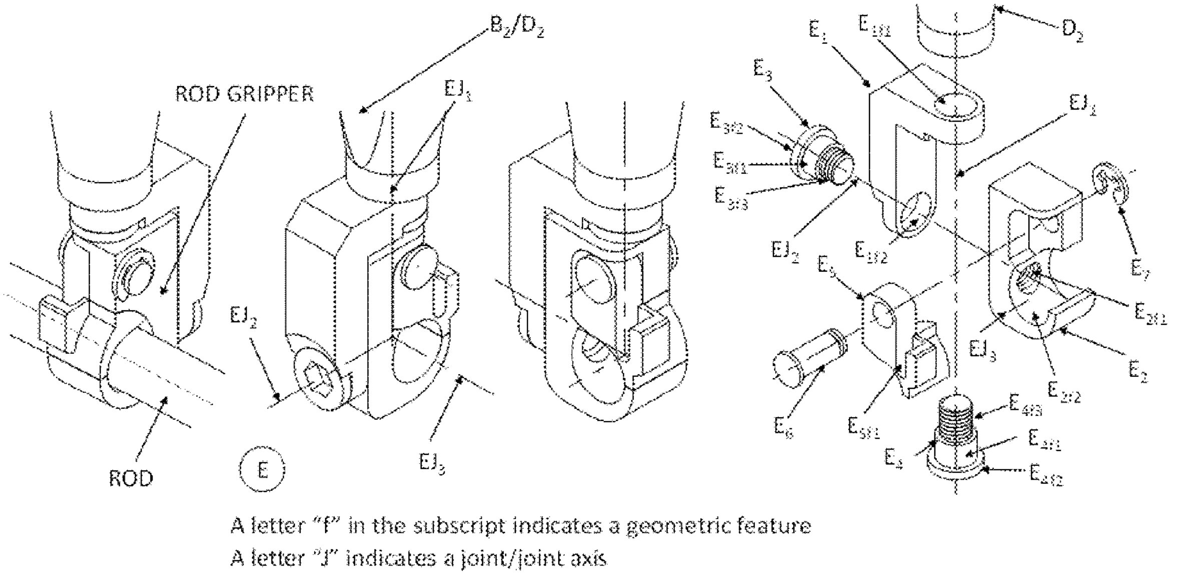
FIG. 11—Perspective view of the assembly of the rod gripper with the locking jaw closed.
Figure 12:
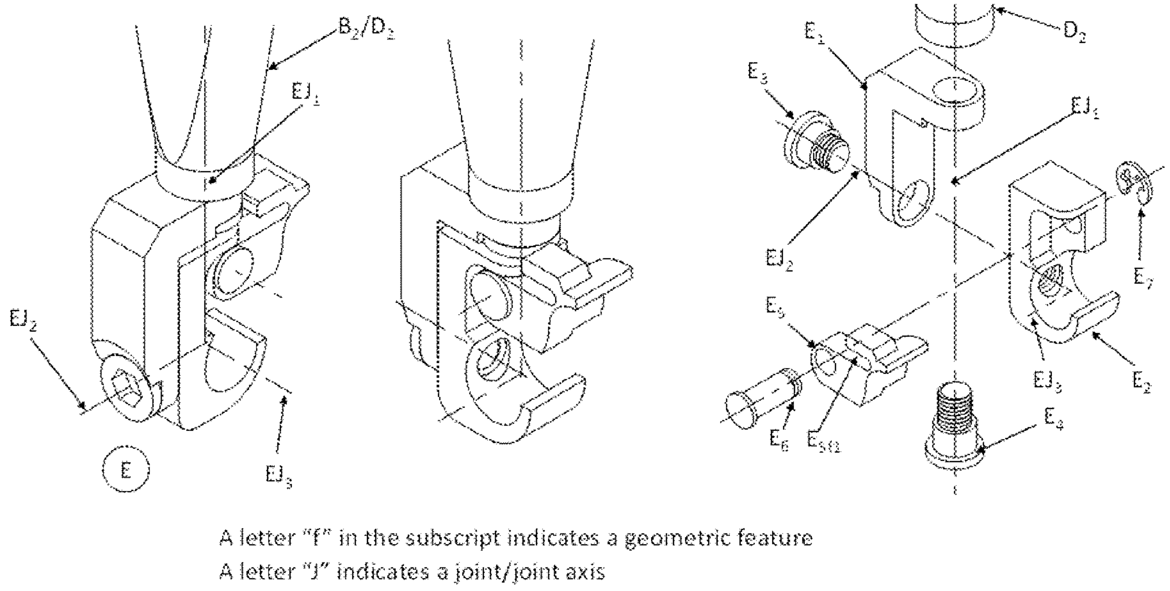
FIG. 12—Perspective view of the assembly of the rod gripper with the locking jaw opened.

With reference to FIG. 11 and FIG. 12, the rod gripper assembly comprises a proximal member $E_1$, a receiving jaw $E_2$, screw pins $E_3$ and $E_4$, and locking jaw $E_5$. Each screw pin has a smooth pin portion, a stopping shoulder at one end of the smooth pin portion and a threaded portion at the other end of the smooth pin portion. The threaded portion $E_{4f3}$ of the screw pin $E_4$ goes through the hole $E_{1f1}$ of the proximal member $E_1$ and is threaded and tight-fit into a tapped hole of the telescopic or auxiliary arm, resulting in a revolute joint around the axis $EJ_1$ between the proximal member $E_1$ and the telescopic or auxiliary arm. The threaded portion $E_{3f3}$ of the screw pin $E_3$ goes through the hole $E_{1f2}$ of the proximal member $E_1$ and is threaded and tight-fit into the tapped hole $E_{2f1}$ of the receiving jaw $E_2$, resulting in a revolute joint around the axis $EJ_2$ between the proximal member $E_1$ and the receiving jaw $E_2$. The receiving jaw $E_2$ has a hook-like shape with a partial cylindrical inner surface $E_{2f2}$ to receive a rod. The locking jaw $E_5$ is mounted on the receiving jaw $E_2$ with a revolute joint using the pin $E_6$ and retaining ring $E_7$.

Figure 13:
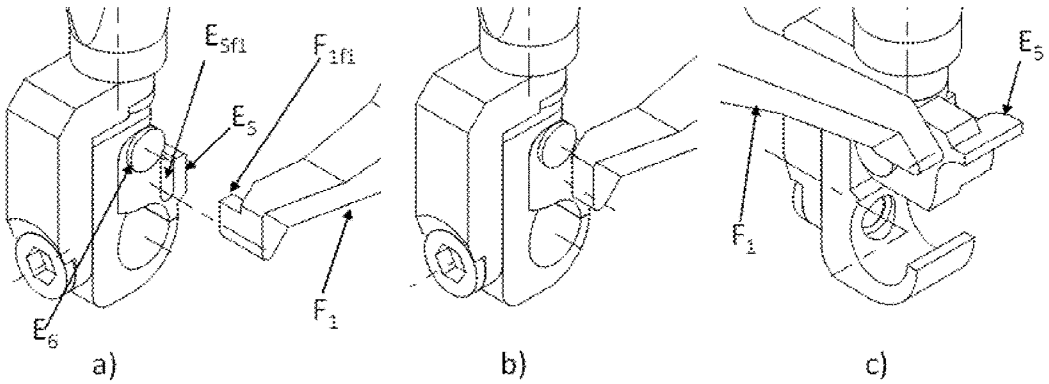
FIG. 13—Illustration of the rod gripper operation.

With reference to FIG. 13, the opening and closing of the locking jaw $E_5$ is operated using the jaw-driver $F_1$. The locking jaw $E_5$ features a recess $E_{5f1}$ and the jaw-driver $F_1$ features a protrusion $F_{1f1}$ that is shaped, sized and disposed to fit into the recess $E_{5f1}$. Turning the jaw-driver $F_1$ counterclockwise around the pin $E_6$ lifts up and opens the locking Jaw $E_5$ to allow a rod to be seated in and mated with the inner cylindrical portion $E_{2f2}$ of the receiving jaw $E_2$ (FIG. 11). Turning the jaw-driver $F_1$ clockwise around the pin $E_6$ pushes down and closes the locking Jaw $E_5$ to prevent the rod from disengaging from the receiving jaw.

Figure 14:
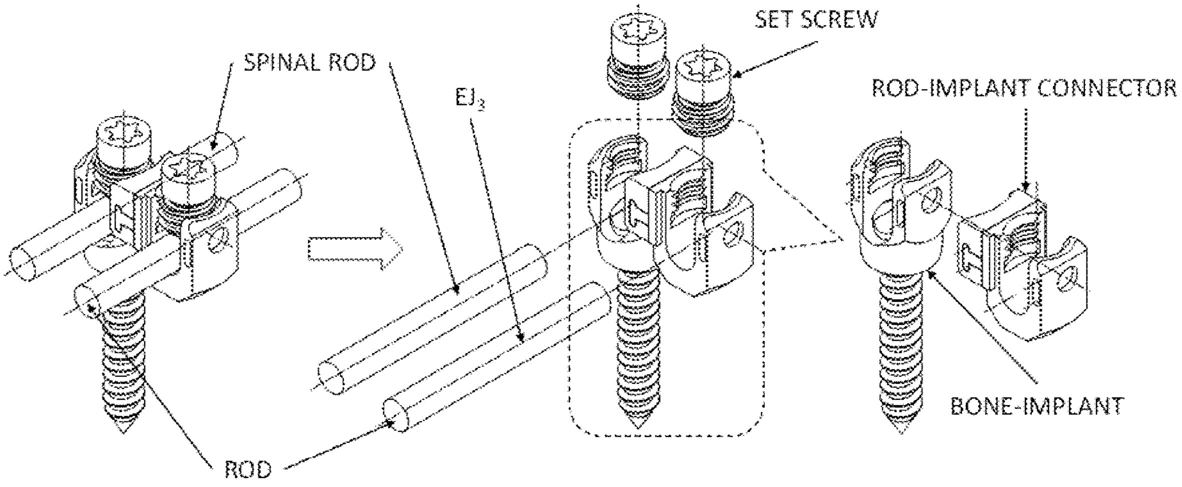
FIG. 14—Perspective view of the assembly of bone implant, spinal rod, rod-implant connector, and rod.

With reference to FIG. 14, the rod is connected to the spine through rod-implant connectors and commonly used bone-implants, which feature an implant head having a center pocket on one side and two lateral recesses respectively on two other sides adjacent to the center pocket side.

Figure 15:
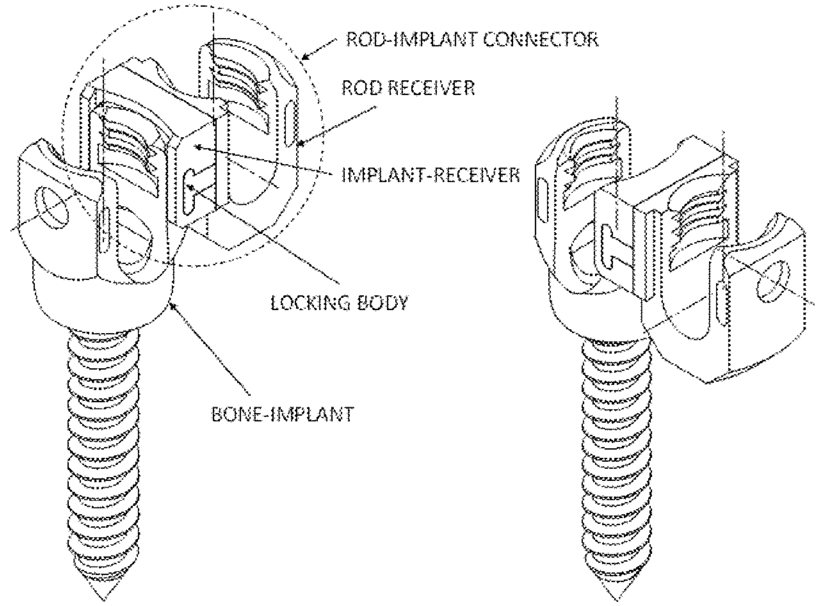
FIG. 15—Perspective view of the assembly of bone-implant and rod-implant connector.
Figure 16:
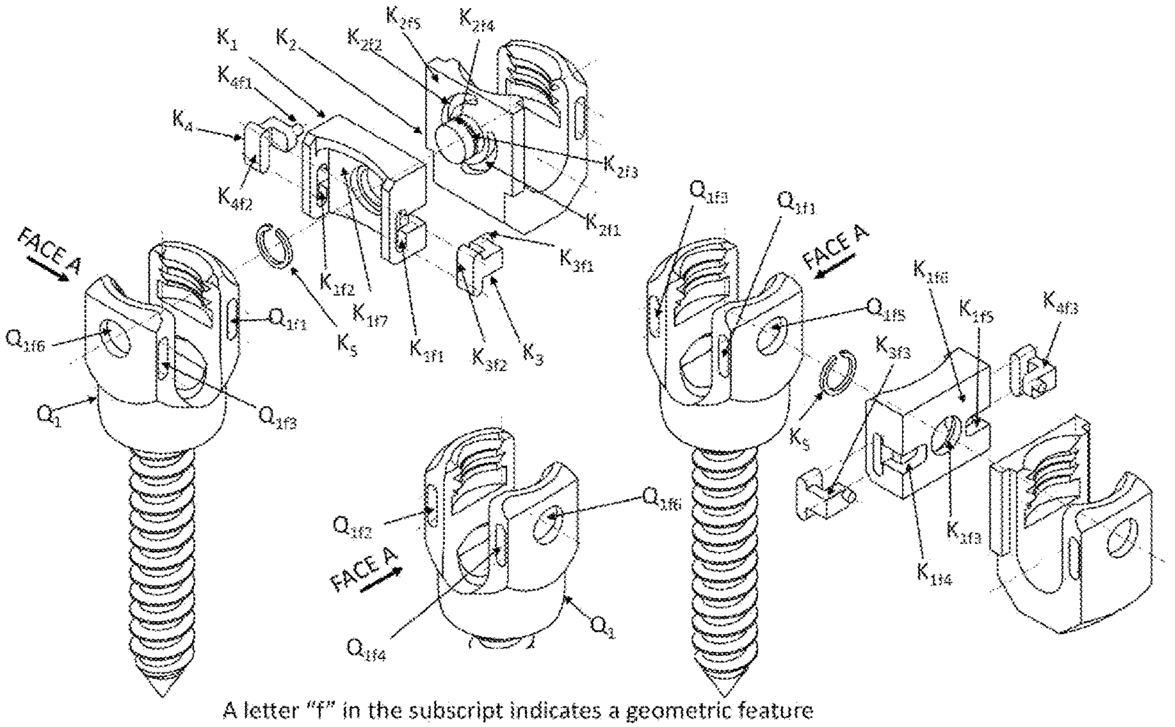
FIG. 16—Exploded perspective view of the assembly of bone-implant and rod-implant connector.

With reference to FIG. 15 and FIG. 16, the rod-implant connector comprises an implant receiver member, a rod receiver member, and two locking bodies. When assembled together with the bone-implant, the implant receiver member is sandwiched between the bone-implant and the rod-receiver member. The head $Q_1$ of a commonly used bone-implant features a center pocket $Q_{1f5}$ (a center pocket $Q_{1f6}$ on the opposite side) and two lateral recesses $Q_{1f1}$ and $Q_{1f2}$. The surface $K_{1f7}$ of the implant receiver member $K_1$ is shaped and sized to mate with the bone-implant on the side of the center packet $Q_{1f5}$ and the sides of the two lateral recesses $Q_{1f1}$ and $Q_{1f2}$ of the bone-implant $Q_1$. The surface $K_{1f6}$ of the implant receiver member $K_1$ is a flat surface, which is in contact with the flat surface $K_{2f5}$ on the rod receiver member $K_2$.

Figure 17:
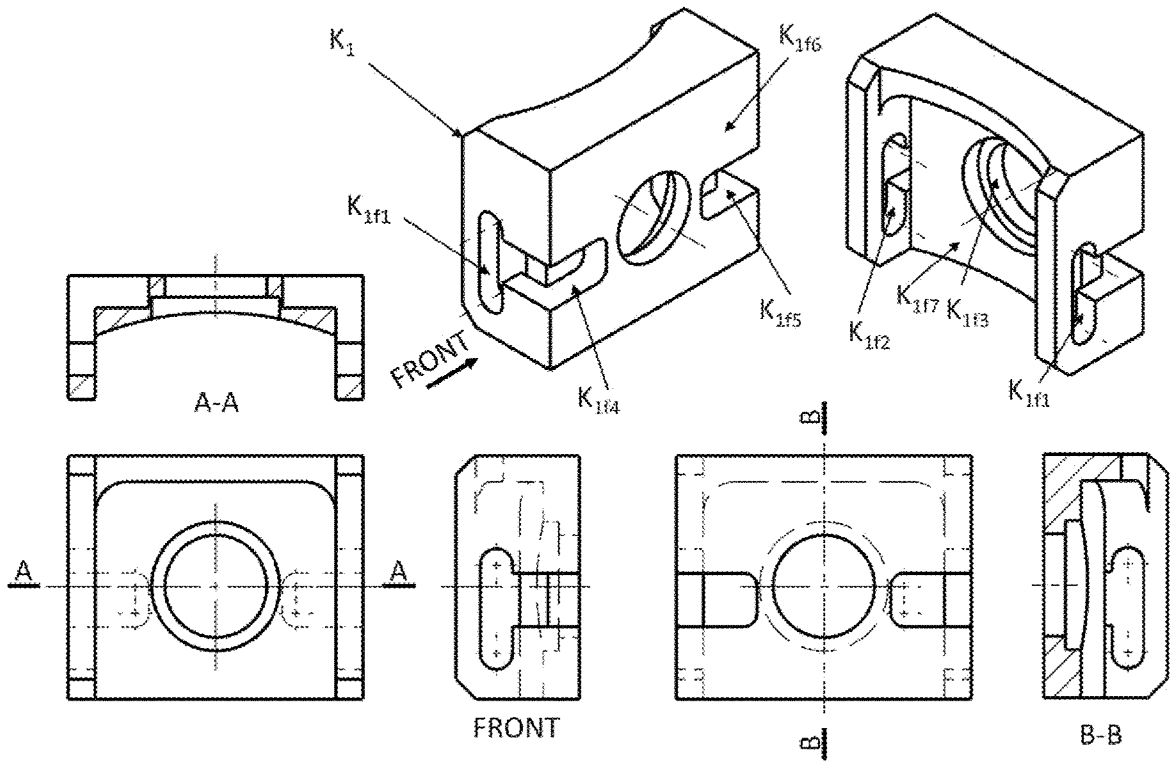
FIG. 17—Perspective and orthographic views of the implant-receiver member of the rod-implant connector.
Figure 18:
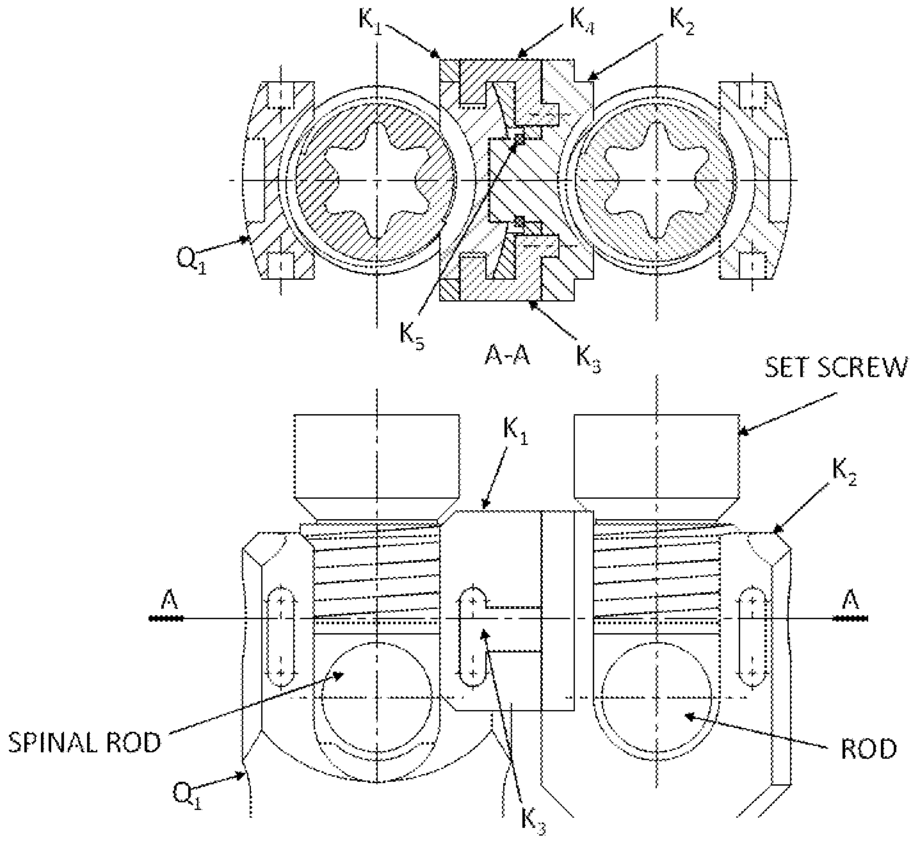
FIG. 18—Cross section view of the assembly of the rod-implant connector and bone implant.

The implant receiver member $K_1$ has a center opening $K_{1f3}$ and the rod receiver member $K_2$ has a center cylindrical protrusion $K_{2f4}$ with a circular groove $K_{2f3}$ in the midway; they are shaped, sized, and disposed such that the protrusion $K_{2f4}$ mates with both the center opening $K_{1f3}$ of the implant receiver $K_1$ and the center pocket $Q_{1f5}$ of the bone-implant $Q_1$, and the retaining ring $K_5$ is mounted into the circular groove $K_{2f3}$ to form a revolute joint between the implant receiver member $K_1$ and the rod receiver member $K_2$ (FIG. 17 and FIG. 18).

With reference to FIG. 16 and FIG. 17, the implant receiver member $K_1$ has two lateral openings $K_{1f1}$ and $K_{1f2}$ sized, shaped, and disposed to be aligned respectively with the two lateral recesses $Q_{1f1}$ and $Q_{1f2}$ of the bone-implant $Q_1$ enabling the implant receiver member $K_1$ to be latched and thus fastened onto the bone-implant $Q_1$.

With reference to FIG. 17, on the flat surface $K_{1f6}$ of the implant receiver member $K_1$, two straight grooves $K_{1f4}$ and $K_{1f5}$ are made in two radial directions of the center opening $K_{1f3}$.

Figure 19:
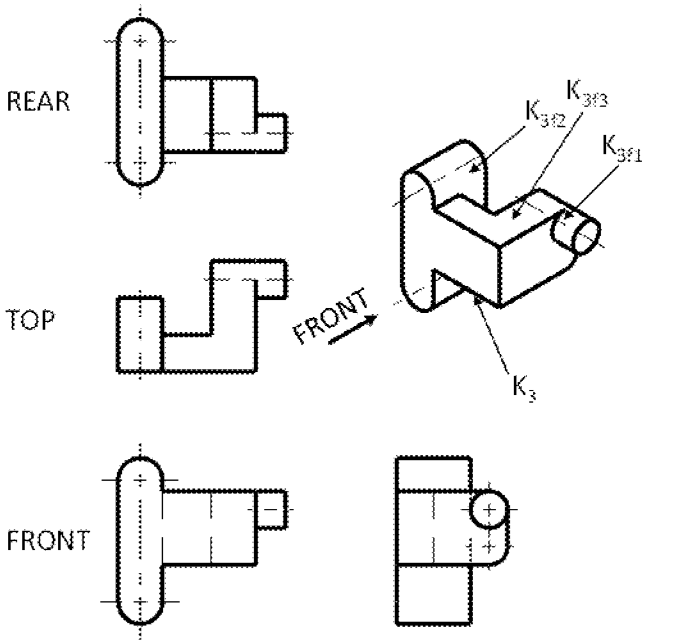
FIG. 19—Perspective and orthographic views of the locking body of the rod-implant connector.
Figure 20:
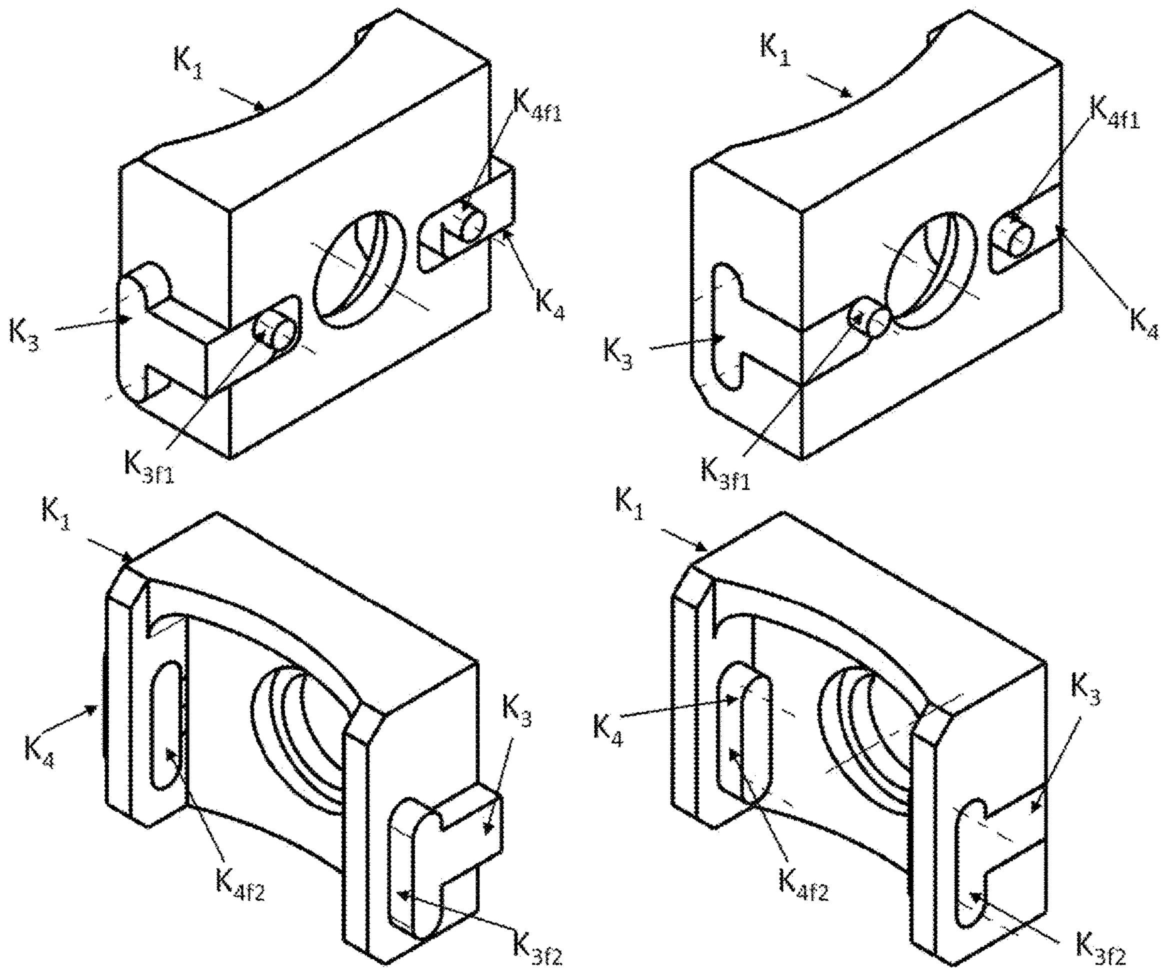
FIG. 20—Perspective view of the assembly of the implant receiver member and the locking bodies of the rod-implant connector.

With reference to FIG. 19, the portion $K_{3f3}$ of the locking body $K_3$ is shaped and sized such that said portion mates with and slides in the straight groove $K_{1f4}$ of the implant receiver $K_1$ (FIG. 17). The portion $K_{3f2}$ of the locking body $K_3$ is shaped and sized such that this portion slides into and mates with both the lateral opening $K_{1f1}$ of the implant receiver member $K_1$ (FIG. 17 and FIG. 20) and the lateral recess $Q_{1f1}$ of the bone-implant $Q_1$ to latch and thus lock the implant-receiver member $K_1$ onto the bone-implant $Q_1$ (FIG. 16 and FIG. 18).

Figure 21:
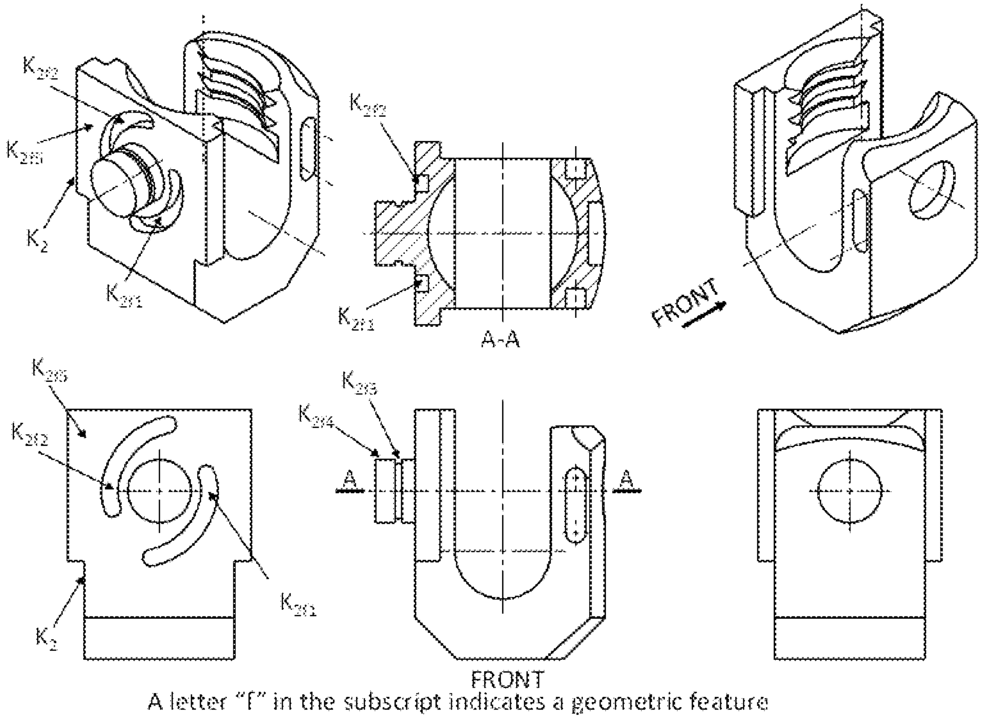
FIG. 21—Perspective and orthographic views of the rod receiver member of the rod-implant connector.

With reference to FIG. 21, on the flat surface $K_{2f5}$ of the rod receiver member $K_2$, two cam grooves $K_{2f1}$ and $K_{2f2}$ are made.

With reference to FIG. 19, the locking body $K_3$ features a protrusion $K_{3f1}$ shaped, sized, and disposed to fit into the cam groove $K_{2f1}$ of $K_2$ (FIG. 21).

Figure 22:
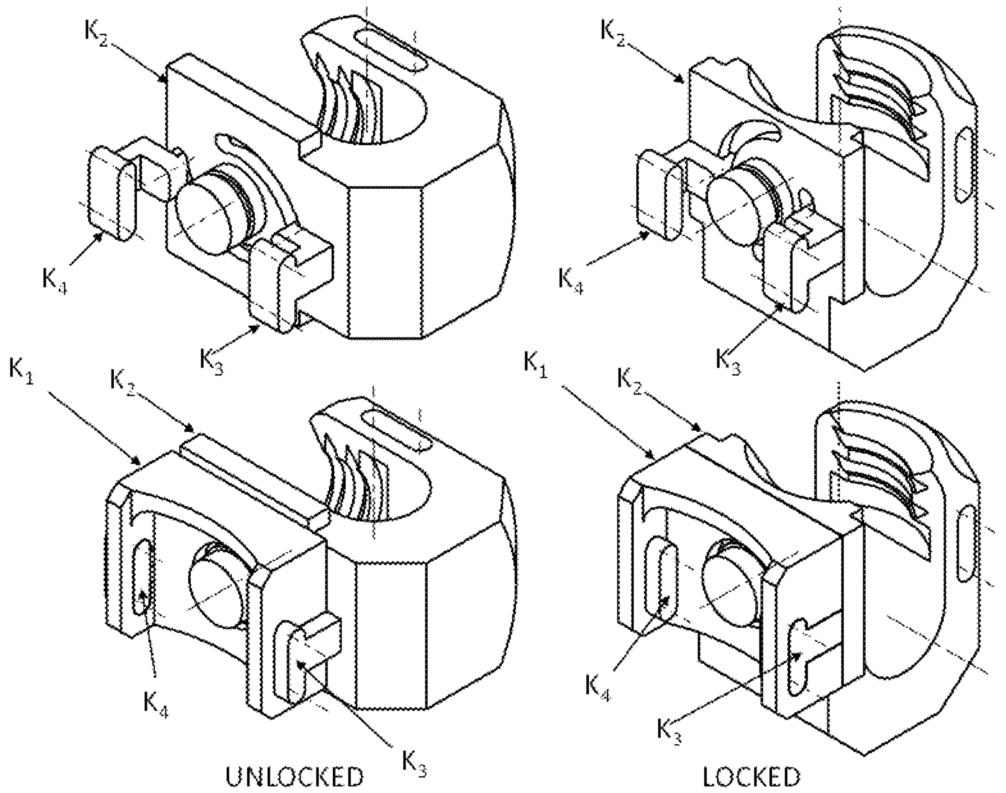
FIG. 22—Perspective view of the assembly of the implant receiver member, the locking bodies, and the rod receiver member of the rod-implant connector.
Figure 23:
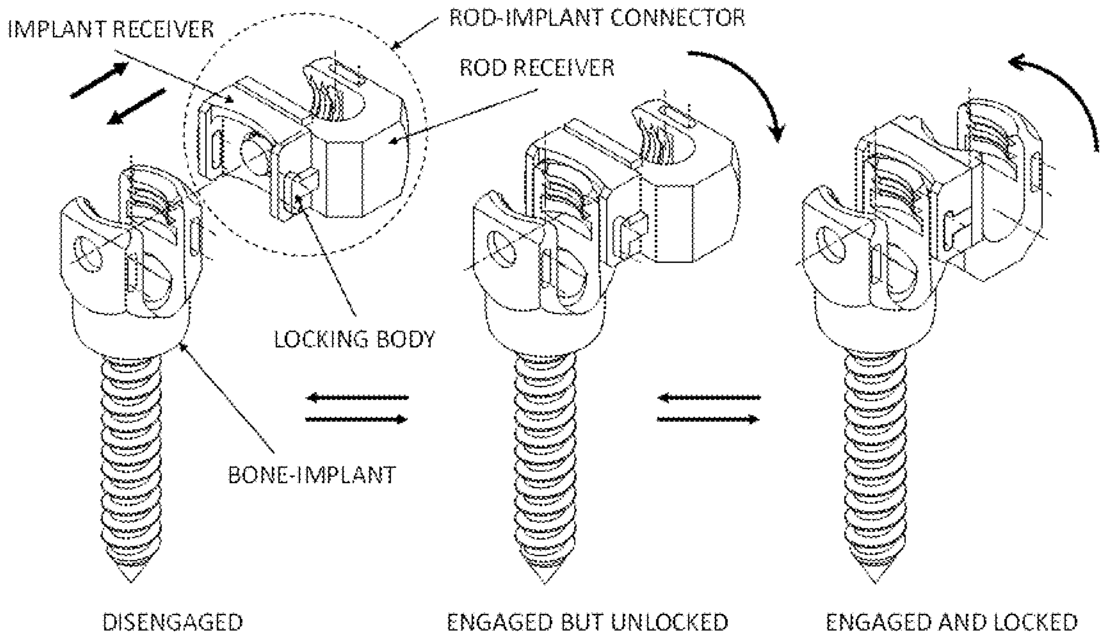
FIG. 23—Perspective view of the assembly of the rod-implant connector.

With reference to FIG. 22, turning the rod receiver member $K_2$ with respect to the implant receiver member $K_1$ clockwise cams the locking bodies $K_3$ and $K_4$ away and disengages them from the lateral recesses of the bone-implant enabling the implant receiver $K_1$ to be separated from the bone-implant; turning the rod receiver member $K_2$ with respect to the implant receiver member $K_1$ counter-clockwise cams the locking bodies $K_3$ and $K_4$ into the lateral recesses of the bone-implant, latches and locks the implant receiver member onto the bone implant (FIG. 23).

Figure 24:
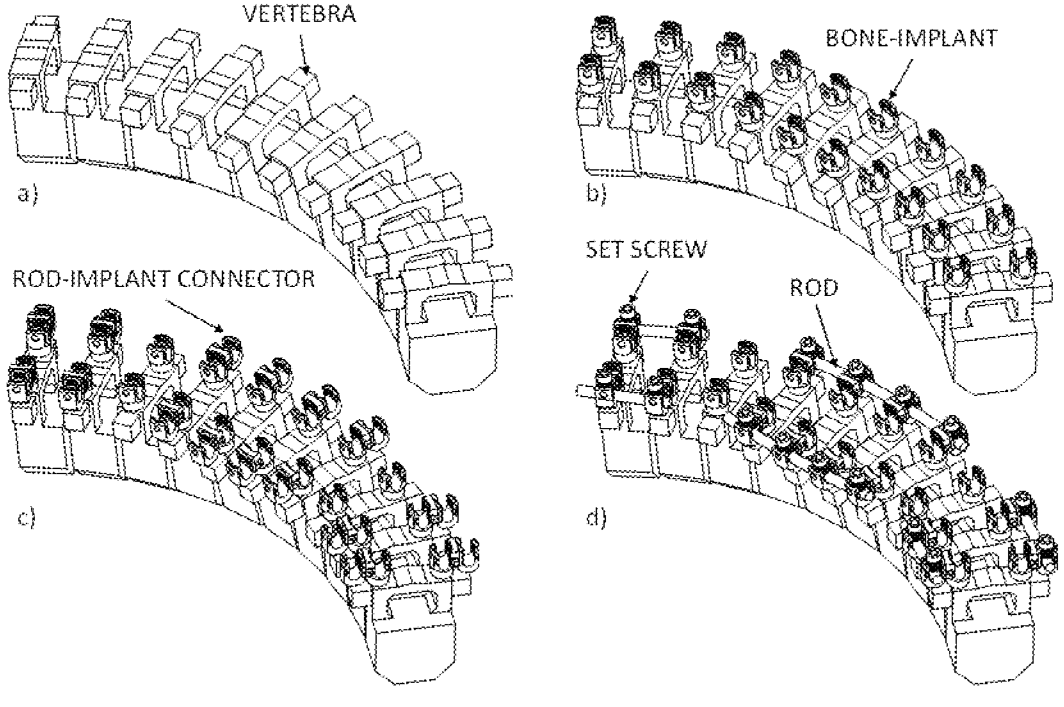
FIG. 24—a) Deformed spinal segment, b) Bone-implant are implanted, c) Rod-implant connectors are connected to bone-implants, d) rods are connected to the rod-implant connectors.
Figure 25:
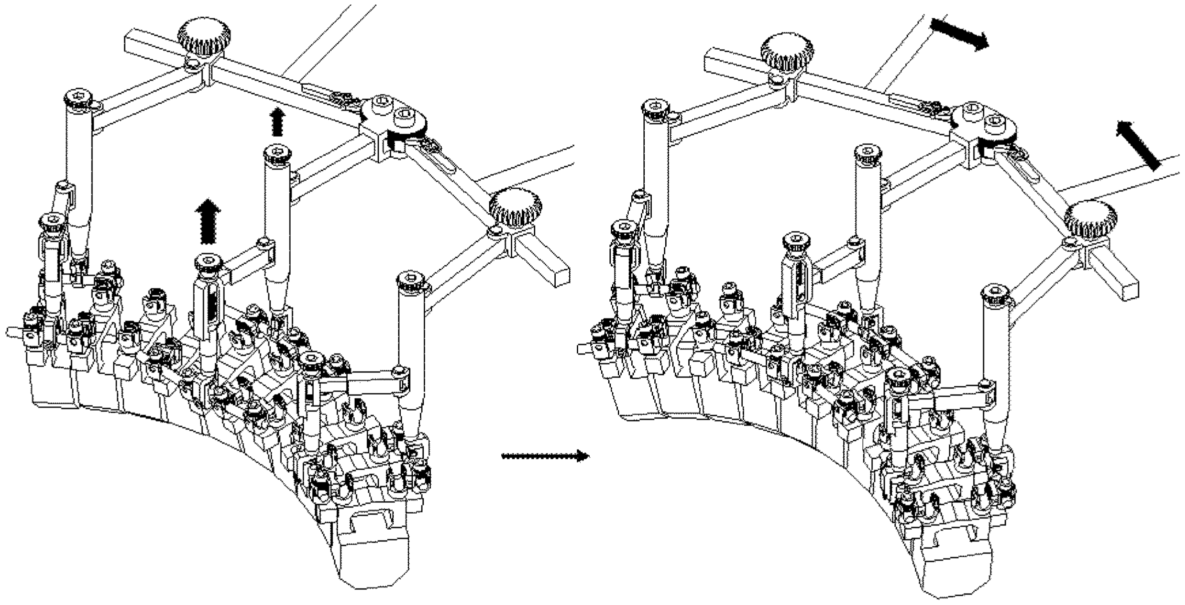
FIG. 25—Sagittal and transverse plane corrections are done by adjusting the lengths of the telescopic arms and the auxiliary arms.
Figure 26:
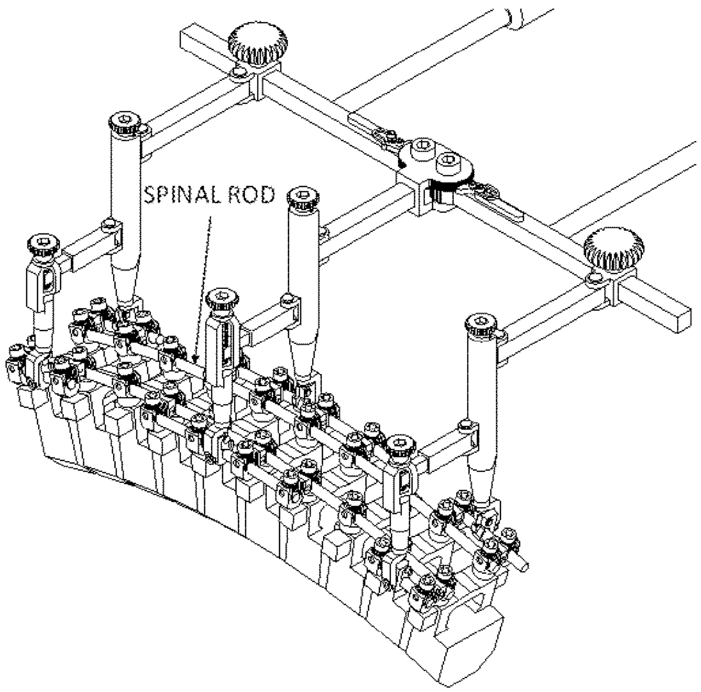
FIG. 26—Coronal plane correction is done by manipulating the angle between the two elongate bodies using the two manipulating handles

After the bone-implants are implanted at the proximal, apical, and distal vertebral levels of the spinal curve, the rod-implant connectors are connected to the bone-implants and the rods are connected to the rod-implant connectors (FIG. 24). The ratchet units are disengaged and the positions of the two transverse arms and the angle between the two elongate bodies are adjusted to the spinal curve to connect the system to the spinal column (FIG. 25). Sagittal and transverse plane corrections are done by adjusting the lengths of the telescopic and auxiliary arms (FIG. 25). Coronal plane correction is done by manipulating the angle between the two elongate bodies using the two manipulation handles (FIG. 26). Once the desired corrections are achieved, the ratchet units are engaged to maintain the corrections. Spinal rods are then contoured to match the alignment of the bone-implants, inserted, and locked on the bone-implants to secure the corrections and allow the system to be disconnected. The system is disconnected from the spinal column when significant spinal stress relaxation is believed to have occurred to maximally reduce the risk of material yielding of the spinal rods.

The invention claimed is:

1. A system for aligning vertebrae to correct spinal deformities, maintaining intraoperative correction, and bearing reaction forces of the spine comprising: a primary motion unit and three telescopic arms; the primary motion unit comprises a center body, two elongate bodies, and two transverse arms; the two elongate bodies are connected respectively to the center body with a revolute joint and extend in opposite directions; the two elongate bodies are coupled by a gear pair with a gear ratio of one to constrain the rotations of the elongate bodies with respect to the center body to be equal and in the opposite directions; the transverse arms each comprise a sliding member and a pivoting member, the pivoting member being connected to the sliding member with a revolute joint; the sliding members of the transverse arms are respectively connected to the elongate bodies with a prismatic or helical joint whose translation can be locked with a locking screw featuring a locking hand wheel; the pivoting members of the transverse arms and the center body of the primary motion unit are respectively connected to the three telescopic arms with a fixed joint.

2. The system of claim 1, wherein the elongate bodies are respectively connected to the center body with a ratchet unit which has an operating handle to be used to engage or disengage the ratchet; the elongate bodies are free to rotate with respect to the center body when both ratchet units are disengaged; when engaged, one ratchet prevents the rotation of the elongate bodies with respect to the center body in one direction; the other ratchet prevents the rotation of the elongate bodies with respect to the center body in the other direction.

3. The system of claim 1, wherein the telescopic arms each comprise: an anchor member and a mobile member connected with a prismatic or helical joint whose translation is controlled with a controlling screw featuring a hand wheel; the anchor member is connected to the pivoting member of the transverse arm or the center body of the primary motion unit with a fixed joint.

4. The system of claim 1 includes three end-effectors respectively connected to the mobile members of the telescopic arms with a revolute joint; the three end-effectors are connected to the spinal column through bone-implants.

5. The end-effector of claim 4 includes a rod gripper, a rod, and a rod-implant connector.

6. The system of claim 1 includes one to three auxiliary arms each comprising: an interconnector, an upper member, and a lower member; the upper member and lower member are connected with a prismatic or helical joint whose translation is controlled with an adjusting screw featuring a hand wheel; the upper member is connected to the interconnector with a prismatic joint; the interconnector is connected to the mobile member of the telescopic arm with a revolute joint; a revolute joint is used to connect the lower member of the auxiliary arm to the proximal member of a rod gripper.

7. A rod gripper assembly for holding a rod and transmitting motion and force to the rod, comprising: a proximal member, two screw pins, a receiving jaw, and a locking jaw; each screw pin has a smooth pin portion, a stopping shoulder at one end of the smooth pin portion and a threaded portion at the other end of the smooth pin portion; the threaded portion of the first screw pin goes through a hole of the proximal member and is threaded and tight-fit into a tapped hole of a mechanical component, resulting in a revolute joint between the proximal member and the mechanical component; the threaded portion of the second screw pin goes through another hole of the proximal member and is threaded and tight-fit into a tapped hole of the receiving jaw, resulting in a revolute joint between the proximal member and the receiving jaw; the receiving jaw has a hook-like shape with a partial cylindrical inner surface to receive a rod; the locking jaw is mounted on the receiving jaw with a revolute joint; using a jaw-driver, the locking jaw is lifted up to allow the rod to be engaged with the receiving jaw from the opening side of the hook-like shape receiving jaw and is closed down with the jaw-driver to prevent the rod from disengaging from the receiving jaw.

8. A rod-implant connector assembly for connecting a rod onto a commonly used bone-implant which features a center pocket on one side and two lateral recesses respectively on two other sides adjacent to the center pocket side, comprising: an implant receiver member, a rod receiver member, and one or two locking bodies; when assembled together with the bone-implant, the implant receiver member is sandwiched between the bone-implant and the rod-receiver member; one side of the implant receiver member is shaped and sized to mate with the bone-implant on the side of the center packet and the sides of the two lateral recesses of the bone-implant; the opposite side of the implant receiver member has a flat surface which is in contact with a flat surface on the rod receiver member; the implant receiver member has a center opening and the rod receiver member has a center cylindrical protrusion with a circular groove in the midway; they are shaped, sized, and disposed such that the protrusion mates with both the center opening of the implant receiver member and the center pocket of the bone-implant, and a retaining ring is mounted into the circular groove to form a revolute joint between the implant receiver member and the rod receiver member; the implant receiver member has two lateral openings sized, shaped, and disposed to be aligned respectively with the two lateral recesses of the bone-implant enabling the implant receiver member to be latched and thus fastened onto the bone-implant; on the flat surface of the implant receiver member in contact with the flat surface of the rod receiver member, two straight grooves are made in two radial directions of the center opening; a portion of each locking body is shaped and sized such that said portion mates with and slides in the straight groove; the portion of each locking body outside the straight groove is shaped, sized, and disposed such that this portion slides into and mates with both the lateral opening of the implant receiver member and the lateral recess of the bone-implant to latch and thus lock the implant-receiver member onto the bone-implant; on the flat surface of the rod receiver member, two cam grooves are made; on each locking body, a protrusion is made to fit into one of the cam grooves; turning the rod receiver member with respect to the implant receiver member clockwise cams the locking bodies away and disengages them from the lateral recesses of the bone-implant enabling the implant receiver to be separated from the bone-implant; turning the rod receiver member with respect to the implant receiver member counterclockwise cams the locking bodies into the lateral recesses of the bone-implant, latches and locks the implant receiver member onto the bone implant.

* * * * *